United States Patent [19]

Cahoy

[11] 4,009,210
[45] Feb. 22, 1977

[54] PROCESS FOR MANUFACTURING 3,5-DITERT.BUTYL-4-HYDROXYBEN-ZALDEHYDE BY FORMYLATION OF 2,6-DITERT.BUTYLPHENOL

[75] Inventor: Roger P. Cahoy, Overland Park, Kans.

[73] Assignee: Gulf Oil Corporation, Pittsburgh, Pa.

[22] Filed: May 7, 1975

[21] Appl. No.: 575,555

[52] U.S. Cl. .......................................... 260/600 R
[51] Int. Cl.² ........................................ C07C 45/00
[58] Field of Search ................................ 260/600

[56] References Cited

UNITED STATES PATENTS 2,903,483  9/1959  Berres ............................. 260/600

*Primary Examiner*—Bernard Helfin
*Attorney, Agent, or Firm*—Carl A. Cline

[57] ABSTRACT

3,5-ditert.butyl-4-hydroxybenzaldehyde is manufactured in good yields by reacting 2,6-ditert.-butylphenol with hexamethylenetetramine or a combination of formaldehyde and ammonium acetate in aqueous acetic acid reaction medium.

3 Claims, No Drawings

PROCESS FOR MANUFACTURING 3,5-DITERT.BUTYL-4-HYDROXYBENZALDE-HYDE BY FORMYLATION OF 2,6-DITERT.BUTYLPHENOL

BACKGROUND OF THE INVENTION 3,5-ditert.butyl-4-hydroxybenzaldehyde is a compound which is useful as a chemical intermediate for manufacture of pesticides of the benzylidenemalononitrile type. There is a need for an uncomplicated process for manufacturing this compound in good yields from inexpensive and readily available starting materials. An attractive starting material for manufacture of the desired product is 2,6-ditert.butylphenol which is a readily available article of commerce. Known procedures for formylation of this compound are too complicated, give only mediocre yields or employ expensive reagents. By way of illustration there has been described by W. Smith [J. Org. Chem. v. 37, 3972–3 (1972)] the reaction of 2,6-ditert.butylphenol with an equimolar quantity of hexamethylenetetramine in trifluoroacetic acid reaction medium. The yield obtained was 60 percent. Hexamethylenetetramine has been employed in the Duff reaction to effect formylation of phenols, but yields are generally low [Chemical Reviews v. 38 p. 230 (1946)].

SUMMARY OF THE INVENTION

I have discovered that 3,5-ditert.butyl-4-hydroxybenzaldehyde is produced in excellent yields by reacting 2,6-ditert.butylphenol with hexamethylenetetramine or a combination of formaldehyde and ammonium acetate in aqueous acetic acid reaction medium.

DESCRIPTION OF THE PREFERRED EMBODIMENTS

The operation of the process of this invention to obtain the desired high yields of product requires use of mole ratios of reactants which favor reaction and the use of aqueous acetic acid of favorable solvent characteristics. The aqueous acetic acid may vary from 65 percent by volume to 85 percent by volume. However, the solvent properties obtained in the range of 75 to 85 percent by volume make this concentration range most convenient, with at least 80 volume percent being preferred. When using freshly prepared acetic acid solvent, use of more than one molar equivalent of hexamethylenetetramine for each mole of phenol is desirable, the use of two to three molar equivalents being preferred. However, when recycled filtrate is employed as solvent medium, the amount of hexamethylenetetramine may be reduced to as low as one molar equivalent without substantial loss of yield, in some instances. This is believed to result from carry-over of unused active reagent in the recycled filtrate.

The use of an elevated temperature, from about 90° to 120° C, is desirable, so as to obtain homogeneous reaction conditions. Reflux temperature at atmospheric pressure is most convenient and effective and is therefore preferred.

The following examples are presented by way of illustration of the process of this invention.

EXAMPLE 1

A twelve liter three-necked round bottomed flask fitted with a power stirrer, pot thermometer, heating mantle, take-off head with thermometer and water cooled condenser was charged with 310 g (1.5 moles) of molten 2,6-ditert.butylphenol, 1300 ml of acetic acid and 420.6 g (3.0 moles) of hexamethylenetetramine. The pot temperature increased from 24° to 36°. The remaining acetic acid charge (1205 ml) caused the pot temperature to increase to 38°. When 495 ml of water was added, the stirred solution formed an emulsion with a small decrease in temperature. With external heating, a clear solution was observed at 93°. When the reaction temperature reached 108°, gentle reflux occurred and carbon dioxide was slowly evolved. After one hour at reflux, fine yellow crystals were observed. After 42 ml of overhead condensate had been collected, the temperature of the reaction mixture increased to 113°. The mixture thickened over the six hour reflux period. The heating mantle was replaced by an ice bath. After cooling to 25°, the reaction mixture was poured on a vacuum filter. The filtrate (2875 ml, 3103 g) was retained. The product cake was transferred to a beaker and stirred for 5 minutes with 3 liters of water. The wash water was removed by means of a porous glass filter-stick. An additional three liters of water was added and the slurry was poured on a vacuum filter. When most of the water has been removed, the product was transferred to a glass tray and dried in the vacuum oven for 5 hours at 60°–65°. There was obtained 317.5 g of light yellow crystalline material, m.p. 187°–89°. By GLC analysis, the product was found to be 100% 3,5-ditert.butyl-4-hydroxybenzaldehyde. The infrared and nuclear magnetic resonance spectra were identical when compared to those of authentic material. The yield was 90%.

The following example is presented to illustrate the use of recycled reaction filtrate as solvent for manufacture of a succeeding batch of product.

EXAMPLE 2

A twelve liter three-necked round bottomed flask equipped as previously described was charged with three liters (3235 g) of recycled reaction filtrate, 210.3 g (1.5 moles) of hexamethylenetetramine and 310 g (1.5 moles) of molten 2,6-ditert.butylphenol. With slow external heating, reflux and carbon dioxide evolution were noted when the pot temperature reached 117°. All reactants had dissolved to give a clear solution. Over fifteen minutes, 20 g of overhead distillate was removed. The pot temperature reached 119° and a yellow crystalline solid began to precipitate. The mixture was refluxed an additional 6 hours. As previously described, the reaction mixture was cooled and the product cake was washed, collected and dried. There was obtained 351.6 g of light yellow crystalline material, m.p. 186°–88°. By GLC analysis, the product was found to be 98.2% 3,5-ditert.buty-4-hydroxybenzaldehyde. The infrared and nuclear magnetic resonance spectra were identical when compared to those of authentic material. The yield was 98.2%.

The effects of varying mole ratios of reactants and acetic acid concentration are illustrated by examples 3 to 14, which were performed according to the procedures illustrated above. The results obtained in these examples are summarized below.

| Ex. No. | Mole of Phenol | Mole of Amine | Vol. % HOAC | Liters of Solvent | Hours Reflux | % yield of Aldehyde |
| --- | --- | --- | --- | --- | --- | --- |
| 3 | 0.05 | 0.1 | 66 | 0.15 | 7 | 44 |

-continued

| Ex. No. | Mole of Phenol | Mole of Amine | Vol. % HOAC | Liters of Solvent | Hours Reflux | % yield of Aldehyde |
|---|---|---|---|---|---|---|
| 4 | 0.1 | 0.2 | 66 | 0.3 | 6 | 44 |
| 5 | 0.1 | 0.2 | 83 | 0.3 | 6 | 85 |
| 6 | 0.1 | 0.2 | 66 | 0.3 | 6 | 33[1] |
| 7 | 0.2 | 0.4 | 83 | 0.6 | 6 | 83 |
| 8 | 0.1 | 0.1 | 83[2] | 0.3 | 6 | 97 |
| 9 | 0.1 | 0.2 | 83 | 0.2 | 3 | 80 |
| 10 | 0.1 | 0.2 | 83 | 0.3 | 6 | 58[3] |
| 11 | 0.1 | 0.2 | 83 | 0.3 | 6 | 66[4] |
| 12 | 0.2 | 0.4 | 83 | 0.4 | 6 | 87 |
| 13 | 0.1 | 0.1 | 83 | 0.3 | 6 | 61 |
| 14 | 0.1 | 0.3 | 83 | 0.3 | 6 | 92 |

[1] 0.1 mole of HCl in the reaction mixture
[2] recycle solvent from example number 7
[3] 0.1 mole of HCl in the reaction mixture
[4] 0.1 mole of NH₄Cl in the reaction mixture The method of this invention has general utility for the conversion of various 2,6-disubstituted phenols to the corresponding 3,5-disubstituted-4-hydroxybenzaldehydes. Examples 15 to 19 were operated employing a phenol to hexamethylenetetramine mole ratio of 1:2 and aqueous acetic acid concentration of 83% by volume in 2 liters of solvent/mole of phenol. The reflux time was 6 hours.

The results are summarized below:

$$\text{HO-}\bigcirc\text{-} \begin{smallmatrix}R\\R'\end{smallmatrix} + (CH_2)_nN_4 \xrightarrow[\text{reflux}]{HOAC-H_2O} \text{HO-}\bigcirc\text{-}\begin{smallmatrix}R\\R'\end{smallmatrix}\text{-CHO}$$

| Example No. | R | R' | % Yield Aldehyde | Melting Point |
|---|---|---|---|---|
| 15 | —Cl | —Cl | 27 | 154–56° |
| 16 | —C(CH₃)₃ | —CH₃ | 69 | 154–56° |
| 17 | —CH(CH₃)₂ | —CH(CH₃)₂ | 95 | 87–90° |
| 18 | —CH₃ | —CH₃ | 83 | 109–12° |
| 19 | —OCH₃ | —OCH₃ | 45 | 112–14° |

Instead of hexamethylenetetramine an equivalent amount of a combination of formaldehyde or a ready source of formaldehyde and ammonia may be employed in the method of this invention. In the strong acetic acid reaction medium the ammonia is present as ammonium acetate. It may be more convenient to use ammonium acetate or another ammonium salt in the reaction rather than to carry out the neutralization of ammonia in the reaction medium. While the reaction with formaldehyde and ammonium acetate appears to be less efficient than the use of hexamethylenetetramine, the lower cost of reagents may more than compensate for the generally lower yields which are obtained.

The use of formaldehyde and ammonia instead of hexamethylenetetramine is illustrated in the examples below.

EXAMPLE 20

A 500 ml reaction flask fitted with a mechanical stirrer, heating mantle, thermometer and water-cooled condenser was charged with 200 ml of glacial acetic acid, and 61.7 g (0.8 mole) of ammonium acetate. To the stirred mixture there were slowly added 97 g of 37% formalin (1.2 moles of formaldehyde) and 20.6 g (0.1 mole) of 2,6-ditert.-butylphenol. The reaction flask was equipped with a take-off head to remove the methanol which is present in commercially available formalin. The mixture was refluxed (107°–9°) for 6 hours. After cooling to ambient temperature, the mixture was poured on a vacuum filter and the product cake was washed with water. After drying, there was obtained 15.8 g of crystalline 3,5-ditert.butyl-4-hydroxybenzaldehyde, m.p. 184°–86° (67.5%).

EXAMPLE 21

A 500 ml reaction flask fitted with a mechanical stirrer, heating mantle, thermometer and water-cooled condenser was charged with 166 ml of glacial acetic acid and 34 ml of water. To the stirred solution were added 61.7 g (0.8 mole) of ammonium acetate, 12 g of paraformaldehyde (0.4 mole equivalent of formaldehyde) and 20.6 g (0.1 mole) of 2,6-ditert.butylphenol. The mixture was refluxed (111°–12°) for 6 hours. After cooling to ambient temperature, the mixture was poured on a vacuum filter and the cake was washed with water. After drying, there was obtained 13.6 g (58%) of impure 3,5-ditert.butyl-4-hydroxybenzaldehyde, m.p. 174°–80°. Following recrystallization from 2-propanol, the yellow crystalline product melted at 188°–90°.

Under similar conditions, 20.6 g (0.1 mole) of 2,6-ditert.butylphenol, 61.7 g (0.8 mole) of ammonium acetate, 36 g (0.4 mole) of s-trioxane in 166 ml of glacial acetic acid and 34 ml of water failed to yield the corresponding aldehyde. However, carbon dioxide (limewater test) was evolved during the 6-hour reflux period. Apparently trioxane is not a satisfactory source of formaldehyde under the disclosed reaction conditions.

The method of this invention finds its principal use in manufacturing 3,5-disubstituted-4-hydroxybenzaldehydes from corresponding 2,6-disubstituted phenols in which the two substituents are methyl or secondary or tertiary hydrocarbon substituents containing up to about 5 carbon atoms, preferably alike. For preparation of aldehydes with other substituents or with unlike substituents the method is less desirable commercially but produces yields which may be adequate for use as laboratory procedures.

I claim:

1. The method of manufacturing 3,5-ditert.butyl-4-hydroxybenzaldehyde comprising reacting a mixture consisting of 2,6-ditert.butylphenol with 2 to 3 molar equivalents of hexamethylenetetramine in at least 80 volume percent aqueous acetic acid at reflux temperature under atmospheric pressure.

2. The method of manufacturing 3,5-ditert.butyl-4-hydroxybenzaldehyde comprising reacting a mixture consisting of 2,6-ditert.butylphenol with at least six molar equivalents of formaldehyde and at least four molar equivalents of ammonium acetate in from 75 to 85 volume percent aqueous acetic acid at reflux temperature under atmospheric pressure.

3. The method of manufacturing 3,5-ditert.-butyl-4-hydroxybenzaldehyde comprising the steps:
   a. reacting a mixture consisting of 2,6-ditert.butylphenol with at least one molar equivalent of hexamethylenetetramine in from 75 to 85 volume percent aqueous acetic acid at reflux temperature under atmospheric pressure;
   b. cooling the reaction mixture and separating the solid product by filtration, and
   c. recycling the filtrate from step (b) to be used as at least a portion of the reaction solvent medium in step (a).

* * * * *